US005141952A

United States Patent [19]

Agouridas et al.

[11] Patent Number: 5,141,952

[45] Date of Patent: Aug. 25, 1992

[54] HETEROCYCLIC DICARBOXYLIC ACIDS

[75] Inventors: Constantin Agouridas, Paris; Patrick Fauveau, Livry-Gargan, both of France

[73] Assignee: Roussel Uclaf, Paris, France

[21] Appl. No.: 716,950

[22] Filed: Jun. 18, 1991

Related U.S. Application Data

[62] Division of Ser. No. 580,213, Sep. 10, 1990, Pat. No. 5,081,135.

[30] Foreign Application Priority Data

Sep. 12, 1989 [FR] France ................................ 89 11879

[51] Int. Cl.$^5$ ..................... A61K 31/35; C07D 309/06

[52] U.S. Cl. .................................... 514/451; 514/460; 549/420; 549/423; 549/425; 549/427

[58] Field of Search ............... 549/420, 423, 425, 427; 514/451, 460

[56] References Cited

U.S. PATENT DOCUMENTS 4,158,635 6/1979 Crutchfield et al. ............... 549/425

*Primary Examiner*—C. Warren Ivy
*Assistant Examiner*—Ba K. Trinh
*Attorney, Agent, or Firm*—Bierman and Muserlian

[57] ABSTRACT

A compound selected from the group consisting of a compound of the formula

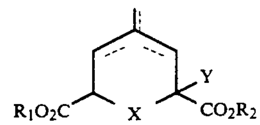

I wherein the dotted lines represent a possible endo or exo double bond, $R_1$ and $R_2$ are individually selected from the group consisting of hydrogen, alkyl of 1 to 8 carbon atoms, alkenyl and alkynyl of 2 to 8 carbon atoms, aryl of 6 to 14 carbon atoms, aralkyl of 7 to 18 carbon atoms and

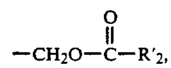

$R'_2$ is alkyl of 1 to 8 carbon atoms or aryl of 6 to 14 carbon atoms, X is —O— or —NR—, R is selected from the group consisting of —OH, hydrogen,

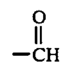

and —COOR′, R′ is hydrogen or alkyl of 1 to 8 carbon atoms, Y is selected from the group consisting of hydrogen, alkyl of 1 to 8 carbon atoms and alkenyl and alkynyl of 2 to 8 carbon atoms, all optionally substituted with at least one halogen or —OH, with the proviso that if Y is —OH, X is not —NH— and their non-toxic, pharmaceutically acceptable addition salts of acids or bases having antibacterial and immunological properties.

14 Claims, No Drawings

HETEROCYCLIC DICARBOXYLIC ACIDS

This application is a divisional of U.S. patent application Ser. No. 580,213 filed Sep. 10, 1990, now U.S. Pat. No. 5,081,135.

STATE OF THE ART

Related prior art includes European Patent Application Ser. No. 0,284,461.

OBJECTS OF THE INVENTION

It is an object of the invention to provide novel compounds formula I and their non-toxic, pharmaceutically acceptable salts of acids and bases and a process for their preparation.

It is another object of the invention to provide novel bactericidal compositions and a method of treating bacterial infections in warm-blooded animals.

These and other objects and advantages of the invention will become obvious from the following detailed description.

THE INVENTION

The novel compounds of the invention are selected from the group consisting of a compound of the formula

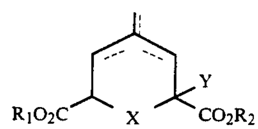

I wherein the dotted lines represent a possible endo or exo double bond, $R_1$ and $R_2$ are individually selected from the group consisting of hydrogen, alkyl of 1 to 8 carbon atoms, alkenyl and alkynyl of 2 to 8 carbon atoms, aryl of 6 to 14 carbon atoms, aralkyl of 7 to 18 carbon atoms and

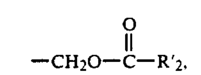

$R'_2$ is alkyl of 1 to 8 carbon atoms or aryl of 6 to 14 carbon atoms, X is —O— or —NR—, R is selected from the group consisting of hydrogen,

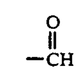

R' is hydrogen or alkyl of 1 to 8 carbon atoms, Y is selected from the group consisting of —OH hydrogen, alkyl of 1 to 8 carbon atoms and alkenyl and alkynyl of 2 to 8 carbon atoms, all optionally substituted with at least one halogen or —OH, with the proviso that if Y is —OH, X is not —NH— and their non-toxic, pharmaceutically acceptable addition salts of acids or bases.

Examples of suitable acids for the formation of acid addition salts are hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkanesulfonic acids such as methane acid or ethanesulfonic acid and arylcarboxylic acids.

Examples of bases for the formation of salts are organic mineral bases such as the alkali metal and alkaline earth metal hydroxides such as sodium hydroxide, potassium hydroxide, lithium hydroxide and calcium hydroxide, magnesium hydroxide or ammonium hydroxide and organic bases such as substituted or non-substituted alkylamines such as trimethylamine, methylamine, propylamine, N,N-dimethylethanolamine or tris(hydroxymethyl) methylamine and basic aminated acids such as lysine or arginine and other bases such as glucosamine or procaine.

Examples of alkyl are methyl, ethyl, propyl, isopropyl and butyl and examples of alkenyl and alkynyl are vinyl, allyl, ethynyl and propynyl. Examples of substituents on alkyl are at least one halogen such as fluorine or chlorine like $—CH_2F$, $—CHF_2$, $—CHCl_2$ and $—CH_2Cl$, aryl such as phenyl or aralkyl such as benzyl.

Among the preferred compounds of the invention are the compounds in which the dotted lines represent an exo double bond as well as those in which the dotted lines do not represent a double bond and their addition salts with organic or mineral acids or with bases.

Among the preferred compounds are those wherein $R_1$ and $R_2$ are hydrogen, those in which Y is hydroxyl radical or acetylene, those wherein X is oxygen atom, those wherein X is $NCO_2R'$, especially wherein X is $NCO_2CH_3$ and their addition salts with organic or mineral acids.

The novel process of the invention for the preparation of compounds of formula I comprises reacting a compound of the formula

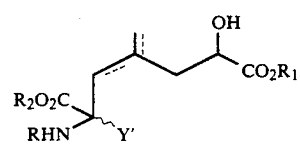

II wherein $R_1$ and $R_2$ have the above definitions, Y' has either the same values as Y, or a precursor of Y and R is CHO or $CO_2$alk and alk is alkyl of 1 to 8 carbon atoms either with a compound of the formula Hal $SO_2$alk III wherein Hal is halogen and alk is alkyl of 1 to 8 carbon atoms to obtain a compound of the formula

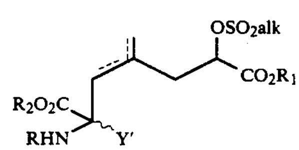

IV reacting the latter with an agent favoring intramolecular nucleophilic substitution to obtain a compound of the formula

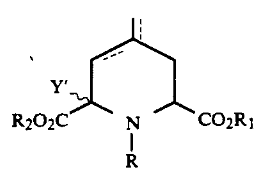

$I_A$ or when Y' is hydrogen and R is CHO, with an agent capable of freeing the aminated function to obtain a compound of the formula

V

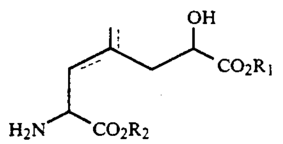

reacting the latter with N-chlorosuccinimide or benzene sulfonate of 4-formyl-1-methyl-pyridininium, subjecting the product to the action of a base and then to the action of a hydrolysis agent to obtain a compound of the formula $I_B$

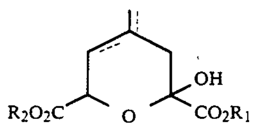

or when Y' is hydrogen and R is CHO with an oxidizing agent to obtain a compound of the formula $I_C$

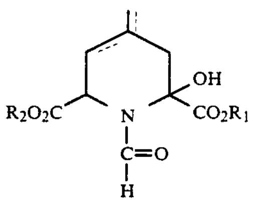

and if appropriate, the compounds of formulae $I_A$, $I_B$ and $I_C$ are subjected, to all or only one of the following operations in any order: possible reduction of the endo or exo double bond; treatment of Y' to obtain Y; total or selective reduction of Y when this is unsaturated; deprotection of the aminated function; and salification.

In a preferred embodiment of the process of the invention, the compound of formula III is mesyl chloride or tosyl chloride; the agent favoring intramolecular nucleophilic substitution is a base such as potassium carbonate or another alkali metal carbonate; the agent capable of freeing the amine function of the compound of formula II is a strong acid such as hydrochloric acid; the base used is diazabicycloundecene or triethylamine; the hydrolysis agent is oxalic acid; the oxidizing agent reacted with the compound of formula II is JONES reagent or $CrO_3$—$H_2SO_4$, $H_2O$; the hydrolysis of the ester functions is preferably carried out by saponification using a mineral base such as sodium hydroxide or potassium hydroxide optionally followed by a treatment with an acid resin; the protective group of acetylene is a trimethylsilyl group or any other known group; the cleaving agent of the optional trimethylsilyl is potassium fluoride or tetrabutylammonium fluoride or other known means; the hydrogenation catalyst is palladium on activated charcoal either poisoned or not by quinoline; the deprotection of the amine function is carried out with a mineral acid such as hydrochloric acid, or by an organic acid such as trifluoroacetic acid; and the salification is carried out by the addition of an acid or base to the reaction medium.

The compounds of formula II used as starting products can be prepared according to the process described in published European Patents No. 0,284,461 and 0,315,519 and in French Application No. BF 8,905,108. Certain starting compounds which have not been described up until now are described in the experimental part.

In a modification of the process, a compound of the formula $II_A$

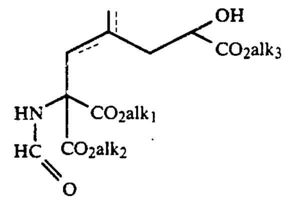

wherein $alk_1$, $alk_2$ and $alk_3$ are individually alkyl of 1 to 8 carbon atoms is reacted with mesyl chloride to obtain a compound of the formula $IV_A$

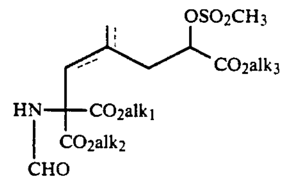

reacting the latter with a cyclization agent to obtain a compound of the formula $I'_A$

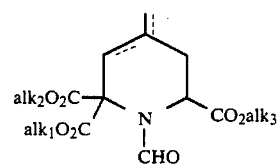

and reacting the latter with a decarboxylation agent to obtain a compound of the formula $I''_A$

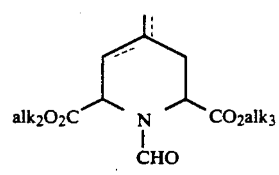

In a preferred embodiment, the decarboxylation is carried out using Krapcho's technique.

In another variation of the process, a compound of the formula $II_B$

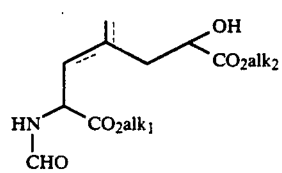

wherein $alk_1$, and $alk_2$ are individually alkyl of 1 to 8 carbon atoms is reacted with an oxidizing agent to obtain a compound of the formula

I'$_C$

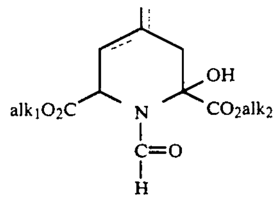

A preferred process comprises reacting a compound of the formula

II$_C$

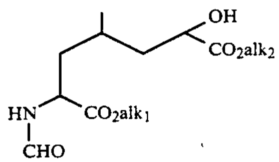

wherein $alk_1$ and $alk_2$ are individually alkyl of 1 to 8 carbon atoms with a deprotection agent of the amine function to obtain a compound of the formula

II'$_B$

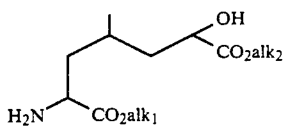

reacting the latter with N-chlorosuccinimide or benzenesulfonate of 4-formyl-1-methyl-pyridinium, then with a base and finally a hydrolysis agent to obtain a compound of the formula

I'$_B$

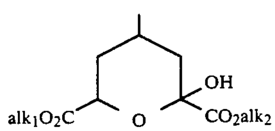

The novel bactericidal compositions of the invention are comprised of a bactericidally effective amount of at least one compound of formula I and their non-toxic, pharmaceutically acceptable salts with acids and bases and an inert pharmaceutical carrier. The compositions may be in the form of tablets, dragees, capsules, granules, suppositories or injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

Due to their antibacterial and immunological properties, the compositions are useful for example, in antibiotherapy vis-a-vis bacterial germs, fungi, yeasts (candida albicans . . . ), as an adjuvant in anti-viral therapy, and in anti-cancer chemotherapy, by themselves or in combination, and finally as adjuvants with a standard anti-biotherapy or with vaccination.

The novel method of treating bacterial infections in warm-blooded animals, including humans, comprises administering to warm-blooded animals a bactericidally effective amount of at least one compound of formula I and their non-toxic, pharmaceutically acceptable salts with bases and acids. The compounds may be administered parenterally, rectally or orally and the usual daily dose is 1,33 to 6,66 mg/kg depending on the condition treated, the specific compound and the method of administration.

In the following examples, there are described several preferred embodiments to illustrate the invention. However, it is to be understood that the invention is not intended to be limited to the specific embodiments.

EXAMPLE 1

1-methyl-2-ethynyl-4-methylene-1,2,6-piperidine-tricarboxylate (isomer A)

STEP A: 1,2-dimethyl-6-ethyl 4-methylene-2-[2-(trimethylsilyl)ethynyl]-1,2,6-piperidine-tricarboxylate (isomers A and B)

2.95 g of potassium carbonate were added to a solution of 10 g of 7-ethyl-1-methyl 6-(methanesulfonyloxy)-2-[(methoxycarbonyl)-amino]-4-methylene-2-[2-(trimethylsilyl)-ethynyl]heptanedioate [described in preparation 1 of BF 8,905,108] and 90 ml of dimethylformamide and the reaction mixture was maintained at 90° C. under an argon atmosphere for 3 hours. The product was diluted with ether and the mineral salts were filtered off. The mixture was evaporated to dryness and the residue was chromatographed on silica eluting with a cyclohexane-ethyl acetate (8-2) mixture to obtain 2.45 g of crude isomer A and 2.72 g of pure isomer B. After a new chromatography on silica and elution with a cyclohexane-ethyl acetate (8-2) mixture, 1.53 g of pure isomer A were obtained. Eluant: cyclohexane-ethyl acetate (8-2); isomer A: Rf=0.26 and isomer B Rf=0.2.

STEP B: 1,2-dimethyl-6-ethyl 2-ethynyl-4-methylene-1,2,6-piperidinetricarboxylate (Isomer A)

0.465 g of potassium fluoride were added to a solution of 1.53 g of the product of Step A (isomer A) in 15 ml of dimethylformamide and the reaction mixture was maintained under agitation for 2 hours. After diluting with ether, the mineral salts were filtered off and the organic phase was washed with salt water, followed by drying and evaporating to dryness to obtain 1.31 g of product which was chromatographed on silica. Elution with cyclohexane, then with a cyclohexane-ethyl acetate (8-2) mixture yielded 1.016 g of the desired product with a Rf=0.2.

STEP C: 1-methyl 2-ethynyl-4-methylene-1,2,6-piperidinetricarboxylate (Isomer A)

0.41 ml of 2N sodium hydroxide were added to a solution of 103 mg of the product of Step B in 1 ml of ethanol and the reaction mixture was stirred for 24 hours at ambient temperature. 0.1 ml of 2N sodium hydroxide were added and stirring was continued for 24 hours. After concentrating, the pH was adjusted to 6 and purification took place on Dowex 50 W×8 resin to obtain 28 mg of the desired product with a Rf=0.4 (eluant: methylene chloride, methanol, acetic acid 80-20-5).

EXAMPLE 2

1-methyl 2-ethynyl-4-methylene-1,2,6-piperidine tricarboxylate (Isomer B)

STEP A: 1,2-dimethyl-6-ethyl 2-ethynyl-4-methylene-1,2,6-piperidine tricarboxylate Using the procedure of Step B of Example 1, 1,2-dimethyl-6-ethyl 4-methylene-2-[2-(trimethylsilyl)-ethynyl]-1,2,6-piperidine tricarboxylate (Isomer B) was reacted to obtain 1.48 g of the desired product with a Rf=0.15 (cyclohexane, ethyl acetate (8-2)).

STEP B: 1-methyl 2-ethynyl-4-methylene-1,2,6-piperidinetricarboxylate (Isomer B)

4.9 ml of 2N sodium hydroxide were added at 0° C. to a solution of 1.39 g of the product of Step A and 14 ml of ethanol and the reaction solution was stirred for 20 hours at ambient temperature. 1 ml of sodium hydroxide was added and the mixture was stirred for 4 hours at ambient temperature. After diluting with water, Dowex 50 W×8 resin was added until a pH of 1 was reached and was then followed by filtering, rinsing with water, then with ethanol and evaporating to dryness to obtain 1.21 g of crude product which was chromatographed on silica eluting with an ethanol-ammonium hydroxide (8-2) mixture to obtain 610 mg of the desired product with a Rf=0.2.

EXAMPLE 3

1-methyl 2-ethenyl-4-methylene-1,2,6-piperidine tricarboxylate (Isomer A)

STEP A: 1,2-dimethyl-6-ethyl 2-ethenyl-4-methylene-1,2,6-piperidine tricarboxylate 3.57 g of the product of Step B of Example 1 were dissolved at ambient temperature in a mixture of 350 ml of ethanol and 0.35 ml of quinoline and then 3.5 g of palladium at 5% on barium sulfate were added. Hydrogenation took place under 1300 mm of mercury, followed by filtering, rinsing with ethanol and evaporation to dryness to obtain 3.9 g of crude product which was purified by successive chromatography on silica eluting with a cyclohexane-ethyl acetate (8-2) mixture, then by a methylene chloride-ethyl acetate mixture (95-5), then by a cyclohexane-ethyl acetate (8-2) mixture to obtain 1.58 g of the desired product with a Rf=0.15 cyclohexane-ethyl acetate (8-2).

STEP B: 1-methyl 2-ethenyl-4-methylene-1,2,6-piperidine-tricarboxylate (Isomer A)

450 mg of the product of Step A were dissolved in 2.5 ml of ethanol and after chilling, 2.5 ml of sodium hydroxide were added. The mixture was stirred for 24 hours at ambient temperature and after diluting with water and chilling, 50 W×8 Dowex resin was added, followed by filtering, rinsing with water, and evaporating to dryness. After filtering the solution and lyophilizing, 306 mg of crude product were obtained which was chromatographed on silica eluting with an ethanol-ammonium hydroxide (8-2) mixture to obtain 228 mg of the desired product with a Rf=0.3.

EXAMPLE 4

1-methyl 2-ethenyl-4-methylene-1,2,6-piperidine-tricarboxylate (Isomer B)

STEP A: 1,2-dimethyl-6-ethyl 2-ethenyl-4-methylene-1,2,6-piperidine tricarboxylate 1.55 g of the product of Step A of Example 2 were dissolved in 150 ml of ethanol and 0.16 ml of quinoline and 1.49 g of palladium at 5% on barium sulfate were added to this solution. The suspension was stirred under a hydrogen atmosphere until absorption of the theoretical volume. Filtration took place followed by rinsing with ethanol and evaporating to dryness to obtain 1.6 g of product which was chromatographed on silica and eluted with a cyclohexane-ethyl acetae (8-2) mixture to obtain 1.08 g of the desired product with a Rf=0.15.

STEP B: 1-methyl 2-ethenyl-4-methylene-1,2,6-piperidine-tricarboxylate (Isomer B)

936 mg of the product of Step A were dissolved in 10 volumes of ethanol and after chilling, 10 volumes of sodium hydroxide were introduced. The mixture was stirred for 48 hours and the solution was then diluted with water. Dowex 50 W×8 resin was added until a pH of 2 was reached and the mixture was stirred for 2 hours at ambient temperature, followed by rinsing with water, concentrating and lyophilizing to obtain 830 mg of product which was purified by chromatography on silica and eluting with an ethanol-ammonium hydroxide (8-2) mixture, then with water. After lyophilizing, 400 mg of the desired product were obtained with a Rf=0.2.

EXAMPLE 5

1-formyl-4-methylene-2,6-piperidine dicarboxylic acid (Isomer A)

STEP A: Triethyl 1-(formylamino)-5-(methanesulfonyloxy)-3-methylene-1,1,5-pentane tricarboxylate Using the procedure of Step A of Example triethyl 1-(formylamino)-5-hydroxy-3-methylene-1,1,5-pentatricarboxylate (prepared as in French Patent No. 2,611,721, preparation B) was reacted to obtain the product.

STEP B: Triethyl 1-formyl-4-methylene-2,2,6-piperidine tricarboxylate

Using the procedure of Step B of Example 1, 10 g of the compound of Step A were reacted to obtain 6.95 g of the desired product with a Rf=0.3 eluant cyclohexane-ethyl acetate (7-3).

STEP C: Diethyl 1-formyl-4-methylene-2,6-piperidine dicarboxylate

A mixture of 5 g of the product of Step B, 0.8 g of sodium chloride, 0.26 g of water and 15 ml of dimethylsulfoxide was stirred for 3 hours at 165° C. and the mixture was returned to ambient temperature followed by filtering, washing and evaporating to dryness to obtain 4 g of product which was purified on silica eluting with a cyclohexane-ethyl acetate (9-1) mixture, then by a cyclohexane-ethyl acetate (7-3) mixture to obtain 3.1 g of the desired product with a Rf=0.5.

STEP D: 1-formyl-4-methylene-2,6-piperidine dicarboxylic acid (Isomer A)

Using the procedure of Step D of Example 1, 997 mg of the product of Step C were reacted to obtain 404 mg of the desired product with a Rf=0.2, eluant ethanol-ammonium hydroxide (8-2).

EXAMPLE 6

Diethyl cis (+) 4-methylene-2,6-piperidine dicarboxylate of diethyl hydrochloride STEP A: Diethyl 4-methylene-2,6-piperidine dicarboxylate (cis isomer and trans isomer)

1.5 ml of 12N hydrochloric acid were added to a solution of 2.8 g of the product of Step C of Example 5 and 30 ml of ethanol and the reaction mixture was refluxed for 2 hours. After evaporation to dryness, the residue was taken up in ethyl acetate and washed with 10% sodium bicarbonate. The organic phase was dried, filtered and evaporated to dryness to obtain 2.0 g of product which was purified on silica eluting with a cyclohexane-ethyl acetate (8-2) mixture to obtain 0.730 g of the cis product and 0.980 g of the trans product.

STEP B: cis diethyl (+) 4-methylene-2,6-piperidine dicarboxylate hydrochloride 2 ml of a solution of 2N hydrochloric acid in ether were added to a solution of 0.2 g of the cis isomer product of Step A in 5 ml of ethyl ether and after evaporation to dryness, the residue was taken up in isopropyl ether, followed by filtering and rinsing with isopropyl ether to obtain 0.205 g of the desired product melting at 166° C.

EXAMPLE 7

Trans diethyl (+) 4-methylene-2,6-piperidine dicarboxylate hydrochloride

Using the procedure of Step B of Example 6, the trans isomer base of Example 6 was reacted to obtain 0.19 g of the desired trans isomer salt melting at 109° C.

EXAMPLE 8

(+) trans 4-methylene-2,6-piperidine dicarboxylic acid 4.3 ml of a solution of 1N sodium hydroxide were added to a solution of 10 ml of ethanol and 0.5 g of the trans product of Step A of Example 6. The reaction mixture was stirred for one hour and after appropriate treatments, 0.23 g of the desired product melting at >250° C. were obtained.

EXAMPLE 9

(+) cis 4-methylene-2,6-piperidine dicarboxylic acid 3.5 ml of a solution of 1N sodium hydroxide were added to a solution of 0.4 g of the cis product of Step A of Example 6, and 10 ml of ethanol were reacted to obtain after appropriate treatments, 0.240 g of the desired product melting at >250° C.

EXAMPLE 10

(+)trans 1-methyl-4-methylene-1,2,6-piperidine tricarboxylate

STEP A: 2,6-diethyl-1-methyl (trans +) 4-methylene-1,2,6-piperidine tricarboxylate 0.346 ml of triethylamine were added at 0° C. to a solution of 6 ml of methylene chloride and 595 mg of the trans product of Example 6, Step A, and 1.76 ml of methyl chloroformate. The solution was stirred at ambient temperature for 3 hours, then diluted with methylene chloride, washed with salt water, dried and evaporated to dryness to obtain 680 mg of product which was chromatographed on silica eluting with a cyclohexane-ethyl acetate (75-25) mixture to obtain the desired product with a Rf=0.3.

STEP B: Trans 1-methyl (+) 4-methylene-1,2,6-piperidine tricarboxylate 1.45 ml of 2N sodium hydroxide were introduced at 0° C. into a solution of 391 mg of the product of Step A and 5 ml of ethanol and the mixture was stirred for 16 hours at ambient temperature. After diluting with water, Dowex w×8 resin was added until a pH of 2 was reached. After appropriate treatments, 157 mg of the desired product were obtained with a Rf=0,25 (ethanol-ammonium hydroxide 8-2).

EXAMPLE 11

(cis +) 1-methyl-4-methylene-1,2,6-piperidine tricarboxylate

STEP A: 2,6-diethyl-1-methyl (cis +) 4-methylene-1,2,6-piperidine tricarboxylate Using the procedure of Step A of Example 10, 595 mg of the cis product of Example 6 were reacted to obtain after chromatography on silica eluting with cyclohexane-ethyl acetate (9-1) 480 mg of the desired product with a Rf=0.25 cyclohexane-acetone (8-2).

STEP B: (cis +) 1-methyl-4-methylene-1,2,6-piperidine tricarboxylate

Using the procedure of Step B of Example 10, 432 mg of the product of Step A were reacted to obtain 132 mg of the desired product with a Rf=0.1 methylene chloride-methanol-acetic acid (95-5-5).

EXAMPLE 12

2-(difluoromethyl)-1-formyl-4-methylene-2,6-piperidine carboxylic acid

STEP A: Ethyl 2-difluoromethyl-1-formyl-4-methylene-2,6-piperidinedicarboxylate 0.39 g of potassium carbonate were added to a solution of 1 g of diethyl 2-(difluoromethyl)-2-(formylamino)-4-methylene-6-(methylsulfonyloxy)-heptanedioate prepared as in Example 12, Step F, of European Patent No. 0,315,519 in 20 ml of dimethylformamide. The suspension was stirred for 90 minutes at 100° C. to obtain after diluting with ethyl ether, filtering and evaporating to dryness, 760 mg of the desired product.

STEP B: 2-(difluoromethyl)-1-formyl-4-methylene-2,6-piperidine dicarboxylic acid 0.68 ml of 1N sodium hydroxide were added to a solution of 54 mg of the product of Step A in 4 ml of ethanol. The mixture was stirred at ambient temperature for 60 hours. 4 ml of water were added and the pH was neutralized to about 6 with Amberlyst 15 resin. After filtering and evaporating to dryness the residue was taken up in 8 ml of water and lyophilized to obtain 47 mg of the desired product in the form of its sodium salt.

EXAMPLE 13

(+) Ethyl 2-difluoromethyl-4-methylene-2,6-piperidine dicarboxylate (Isomer A and Isomer B)

760 mg of the product of Step A of Example 12 were dissolved in 25 ml of ethanol and 4 ml of 12N hydrochloric acid were added. The reaction mixture was stirred for 2 hours 30 minutes at reflux and 5 ml of water were added. The mixture was neutralized with sodium bicarbonate and evaporated to dryness. The residue was taken up in water and extracted three times with ethyl acetate. After drying and evaporating to dryness, 520 mg of product were obtained which was purified by two chromatographies on silica eluting with a cyclohexane-ethyl acetate (9-1) mixture to obtain 225 mg of Isomer A and 185 mg of Isomer B. (Isomer A Rf=0.55 Isomer B Rf=0.50 in cyclohexane-ethyl acetate (6-4)).

EXAMPLE 14

(+) 2-difluoromethyl-4-methylene-2-6-piperidine dicarboxylic acid Isomer (A)

1.2 ml of 2N sodium hydroxide were added to a solution of 200 mg of the product of Example 13 (isomer A) in 7 ml of ethanol and the reaction mixture was stirred for 32 hours at ambient temperature. The pH was taken to about 5 with 2N hydrochloric acid and after evaporating to dryness, the residue was taken up in water, then chromatographed on Dowex resin, eluting with water, then 0.7N ammonium hydroxide, then with water. After evaporation to dryness, 150 mg of crude product were obtained which was taken up in 20 ml of water. After filtering and lyophilizing, 140 mg of the desired product with a Rf=0.4 eluant butanol-acetic acid-water (4-2-2) were obtained.

EXAMPLE 15

(+) 2-difluoromethyl-4-methylene-2,6-piperidine-dicarboxylic acid (Isomer B)

1.3 ml of 2N sodium hydroxide were added to a solution of 190 mg of the product of Example 13 (Isomer B) in 7 ml of ethanol and the mixture was stirred at ambient temperature for 30 hours and then neutralized to about pH 5 with 2N hydrochloric acid. After evaporating to dryness, the residue was taken up in 5 ml of water, then chromatographed on Dowex resin followed by elution with water. After evaporation to dryness, 140 mg of the product were taken up in 200 ml of water, filtered and lyophilized to obtain 130 mg of the desired product with a Rf=0.4 Butanol-acetic acid-water (4-2-2).

EXAMPLE 16

1-methyl 2-methyl-4-methylene-1,2,6-piperidine tricarboxylate (Isomer A)

STEP A 3.6 g of ethyl 2-[(methoxycarbonyl)-amino]-2-methyl-4-methylene-6-(methylsulfonyloxy) heptanedioate prepared as in Example 11, Step E, of European Patent No 0,315,519 were dissolved in 80 ml of dimethylformamide and 1.46 g of potassium carbonate were added. The suspension was stirred vigorously for 4 hours at 100° C. and after diluting with ethyl ether, filtering and evaporating to dryness, 3.7 g of crude product were obtained which was purified by chromatography on silica eluting with a cyclohexane-ethyl acetate-methylene chloride (5-2-3) mixture to obtain 1.05 g of pure Isomer A product and 0.56 g of a mixture. The mixture was chromatographed eluting with a cyclohexane-ethyl acetate-methylene chloride (5-2-3) mixture to obtain 300 mg of Isomer B and 50 mg of Isomer A.

STEP B: 1-methyl 2-methyl-4-methylene-1,2,6-piperidine tricarboxylate (Isomer A)

11.5 ml of 6N sodium hydroxide were added to a solution of 290 mg of the product of Step A in 2 ml of ethanol and the mixture was stirred at ambient temperature for 4 hours. The pH was taken to 3 with Amberlyst 15 resin and after rinsing with water, filtering and evaporation to dryness, 225 mg of crude product were obtained which was chromatographed on silica eluting with an ethanol-ammonium hydroxide 95/5-90/10-80/20 mixture. After taking up in water, filtering and lyophilizing, 95 mg of the desired product with a Rf=0.25 ethanol-ammonium hyroxide (9-1) were obtained.

EXAMPLE 17

1-methyl 2-methyl-4-methylene-1,2,6-piperidine tricarboxylate (Isomer B)

10 ml of 6N sodium hydroxide were added to a solution of 190 mg of the product of Step A of Example 16 (Isomer B) in 2 ml of ethanol and the mixture was stirred for 6 days at ambient temperature. The product was neutralized with Dowex resin and the mixture was rinsed with water until a pH of 3 was reached. After filtering and evaporating to dryness, 122 mg of product were obtained which was purified by chromatography on silica, eluting with a methanol-ammonium hyroxide (80-20) mixture. The product was evaporated to dryness, then taken up in 20 ml of water. After filtering and lyophilizing, 62 mg of the desired product with a Rf=0.2 in ethanol-ammonium hydroxide (9-1) were obtained.

EXAMPLE 18

Diethyl 1-formyl-2-hydroxy-4-methyl-2,6-piperidine dicarboxylate 3.5 ml of Jones reagent [270 g of $CrO_3$, 400 ml of water and 230 ml of $H_2SO_4$ plus sufficient quantity of water to make 1 liter were added to a solution of 3 g of the product of Step B below and 60 ml of acetone and the mixture was stirred for 90 minutes. The excess oxidizing agent was destroyed by the addition of isopropanol. Water was added, and the mixture was neutralized by the addition of potassium carbonate in powder form. Extraction with methylene chloride was effected followed by drying on magnesium sulfate, by filtering and evaporation to dryness under reduced pressure to obtain 3.2 g of product which was chromatographed on silica, eluting with a cyclohexane-ethyl acetate 7-3 mixture to obtain 970 mg of the desired product with a Rf=0.20.

Preparation: Diethyl 2-(formylamino)-6-hydroxy-4-methylene heptanedioate

STEP A: Diethyl 2-(formylamino)-6-hydroxy-4-methylene heptanedioate

A solution of 17.9 g of triethyl 1-(formylamino)-5-hydroxy-3-methylene, 1,1,5-pentane-tricarboxylate prepared as in French Patent Application No. 2,611,721, 300 ml of dimethylformamide, 4.87 g of cesium carbonate and 13.15 g of 4-aminothiophenol was stirred for 3 hours at 95° C. The majority of the dimethylformamide was evaporated off under reduced pressure and 100 ml of ice-water were added. Extraction was effected with methylene chloride, followed by washing with 2N hydrochloric acid and salt water. After drying, filtering and evaporation to dryness under reduced pressure, 15.2 g of product were obtained which was chromatographed on silica eluting with a methylene chloride-methanol (98-2) mixture to obtain 11.06 g of the desired product.

STEP B: Diethyl 2-(formylamino)-6-hydroxy-4-methyl heptanedioate 5.74 g of product of Step A, 150 ml of ethanol, 30 ml of pure acetic acid and 1.5 g of 10% palladium were left for 15 hours under a pressure cf 10 kg of hydrogen. After filtering, rinsing with ethanol and bringing to dryness under reduced pressure, the oily residue was taken up in methylene chloride, decanted, dried and brought to dryness to obtain 5.4 g of the desired product.

EXAMPLE 19

1-formyl-2-hydroxy-4-methyl-2,6-piperidine dicarboxylic acid (sodium salt)

A mixture of 143 mg of the product of Example 18, 2 ml of ethanol and 1 ml of N sodium hydroxide was stirred for 15 hours at ambient temperature to obtain 155 mg of product which was taken up in water, filtered and lyophilized to obtain 146 mg of the desired product with a Rf=0.35 (butanol-acetic acid-ethanol 4-2-2).

EXAMPLE 20

Sodium and 6-ethyl 1-formyl-2-hydroxy-4-methyl-2,6-piperidine dicarboxylate 0.95 ml of N sodium hydroxide were added to a solution of 287 mg of the product of Example 18 and 4 ml of ethanol and the mixture was stirred for 4 hours at ambient temperature then evaporated to dryness under reduced pressure. 5 ml of water were added and extraction took place several times. The aqueous phase was filtered and freeze-dried to obtain 258 mg of the desired product with a Rf=0.45 (butanol-acetic acid-ethanol 4-2-2).

EXAMPLE 21

2-hydroxy-4-methyl-tetrahydro-2H-pyran-2,6-dicarboxlic acid (sodium salt)

STEP A: Diethyl 2-amino-6-hydroxy-4-methyl heptanedioate

A mixture of 2 g of diethyl 2-(formylamino)-6-hydroxy-4-methyl heptanedioate, 20 ml of ethanol and 2 ml of concentrated hydrochloric acid was stirred at 90° C. and after cooling, 10 ml of water were added. Neutralization took place by the addition of solid sodium carbonate and after extracting with methylene chloride, drying, filtering and bringing to dryness, 1.7 g of the desired product with a Rf=0.1 (eluant methylene chloride-ethyl acetate (1-1) were obtained.

STEP B: Diethyl 2-hydroxy-4-methyl-tetrahydro-2H-pyran-2,6-dicarboxylate (Isomer A and Isomer B)

840 mg of 4-formyl-1-methyl pyridinium benzensulfonate were added to a solution of 740 mg of the product of Step A, 15 ml of methylene chloride and 5 ml of dimethylformamide and the reaction mixture was stirred for 45 minutes. 1 ml of diazobicyclo[5,4,0]-undec-7-ene was added and the reaction mixture was stirred for 45 minutes. After cooling down to 5°-10° C., 5 ml of a saturated aqueous solution of oxalic acid were added and the reaction mixture was stirred for 1 hour. Extraction took place with methylene chloride followed by washing with a solution of sodium bicarbonate, drying, filtering and bringing to dryness to obtain 630 mg of product which was chromatographed on silica, eluting with a cyclohexane-ethyl acetate (9-1) mixture to obtain 160 mg of Isomer A and 125 mg of Isomer B.

Isomer A

NMR Spectrum $CDCl_3$ 400 MHz, 0.98 to 1.07 $CH_3$—CH, 1.22 to 1.40 m $CH_3$—$CH_2$, 1.4 to 3.05 m the $CH_2$'s and CH—$CH_3$'s, —4.51 (dd) the 2 types of O—CH—$CH_2$
$CO_2Et$ —4.66 (dd)
—4.6 to 4.40 (m) —$CH_2$—$CH_3$ of $CO_2CH_2CH_3$.

Isomer B:

NMR Spectrum in $CDCl_3$ 400 MHz
—0.99 (d) $\underline{CH_3}$—CH
—1.28 (t) 1.34 (t) $\underline{CH_3}$—$CH_2$
—2.00 (m)
—1.71 (dd) J=13 and 11 Hz
—1.75 (dd) J=13 and 4 Hz } the $CH_2$'s of the ring
—2.14 (m) $CH_3$—$C\underline{H}$—$CH_2$.

STEP C:

2-hydroxy-4-methyl-tetrahydro-2H-pyran-2,6-dicarboxylic acid (sodium salt)

A mixture of 111 mg of a mixture of Isomer A and B of Step B, 3 ml of ethanol and 0.85 ml of N sodium hyroxide was stirred for one night. The mixture was evaporated to dryness under reduced pressure and a few ml of distilled water were added. After filtering and lyophilizing, 91 mg of the desired product were obtained.

NMR $D_2O$ 300 MHz
$CH_3$ 0.96 (d)

$CH_3$
$C\underline{H}_2$, $C\underline{H}$ 1.0 to 2.3 ppm

-continued

| | |
|---|---|
| 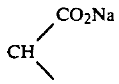 | 4.05 (dd)<br>4.27 (dd)<br>4.44 (dd)<br>4.51 (dd)<br>1.35 (t J=13)<br>1.77 m<br>1.97 m |
| —CH $CO_2$ Na | 4.08 4.27 dd:J=13 |

EXAMPLE 22

Sodium 2-hydroxy-4-methyl-tetrahydro-2H-pyran-2,6-dicarboxylate (Isomer B)

Using the procedure of Step C of Example 21, Isomer B of Step B of Example 21 was reacted to obtain the desired product.

NMR $D_2O$ 300 MHz. $CH_3$ in position 4:0.95 (d J=6.5).

Hydrogens of ring in position 3,4,5:1.15 (q J=13), 1.35 (t J=13), 1.77 (m), 1.97 (m).

Hydrogen of ring in position 6:4.08, 4.27 (dd J=13).

EXAMPLE 23

Sodium 2-hydroxy-4-methyl-tetrahydro-2H-pyran-2,6-dicarboxylate (Isomer A)

Using the procedure of Step C of Example 21, Isomer A of Step B of Example 21 was reacted to obtain the desired product.

NMR $D_2O$ 300 MHz.

$CH_3$ in position 4:0.96 (d J=6.5).

Hydrogens of ring in positions 3,4,5:1.21 (d J=7), 1.25 to 3.0.

Hydrogen of ring in position 6:4.08, 4.27.

EXAMPLE 24

Tablets were prepared containing 50 mg of the product of Example 1 and sufficient excipient for a tablet of 250 mg of lactose, starch, talc and magnesium stearate

EXAMPLE 25

Capsules were prepared containing 100 mg of the product of Example 21 and a standard excipient for capsules Antibacterial activity (in vitro)

The antibacterial activity of the claimed products was determined by the diffusion method in Davis Mingioli medium with 1% agar added. The geloses used were poured into Petri dishes at 48° C., after seeding at $5\times10^5$ germs/ml using the test bacterial strain. The inocula came from a 24 hour pre-culture in a Davis Mingioli culture medium. After hardening the geloses, the aqueous solutions of the studied products were introduced into 9 mm wells hollowed out in the medium using a hollow punch. The observed inhibition zones (diameter in mm) were measured after incubation for 24 hours at 37° C.

| | Product of Example 1 (100 mg/l) | Product of Example 2 (100 mg/l) | Product of Example 22 (100 mg/l) |
|---|---|---|---|
| *Escherichia coli* 078 | 17.5 | 18 | |
| *Salmonella typhimurium* MZ11 | 31 | 34 | 19 |
| *Enterobacter cloacae* 1321E | 26 | 29 | |
| Providencia sp. DU48 | 29 | 28 | |

Various modifications of the products and method of the invention may be made without departing from the spirit or scope thereof and it should be understood that the invention is intended to be limited only as defined in the appended claims.

What is claimed is:

1. A compound selected from the group consisting of a compound of the formula

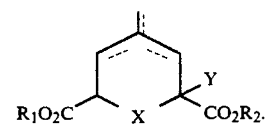

I wherein the dotted lines represent an optional endo or exo double bond, $R_1$ and $R_2$ are individually selected from the group consisting of hydrogen, alkyl of 1 to 8 carbon atoms, alkenyl and alkynyl of 2 to 8 carbon atoms, phenyl, benzyl and

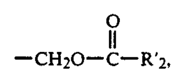

$R'_2$ is alkyl of 1 to 8 carbon atoms or aryl of 6 to 14 carbon atoms, X is —O—, Y is —OH and their non-toxic, pharmaceutically acceptable acid addition salts of acids and bases.

2. A compound of claim 1 wherein the dotted lines are an exo double bond.

3. A compound of claim 1 wherein the dotted lines are not a double bond.

4. A compound of claim 1 wherein $R_1$ and $R_2$ are hydrogen.

5. A compound of claim 1 wherein R' is —$CH_3$.

6. A bactericidal composition comprising a bactericidally effective amount of at least one compound of claim 1 and an inert pharmaceutical carrier.

7. A composition of claim 6 wherein the dotted lines are an exo double bond.

8. A composition of claim 6 wherein the dotted lines are not a double bond.

9. A composition of claim 6 wherein $R_1$ and $R_2$ are hydrogen.

10. A composition of claim 6 wherein R' is —$CH_3$.

11. A method of treating bacterial infections in warm-blooded animals comprising administering to warm-blooded animals a bactericidally effective amount of at least one compound of claim 1.

12. A method of claim 11 wherein the dotted lines are not a double bond.

13. A method of claim 11 wherein $R_1$ and $R_2$ are hydrogen.

14. A method of claim 11 wherein R' is —$CH_3$.

* * * * *